United States Patent
Hashimoto et al.

(10) Patent No.: US 10,959,795 B2
(45) Date of Patent: Mar. 30, 2021

(54) REMOTE-CONTROL MANIPULATOR SYSTEM AND METHOD OF OPERATING THE SAME

(71) Applicant: KAWASAKI JUKOGYO KABUSHIKI KAISHA, Kobe (JP)

(72) Inventors: Yasuhiko Hashimoto, Kobe (JP); Masayuki Kamon, Akashi (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 301 days.

(21) Appl. No.: 15/755,112

(22) PCT Filed: May 27, 2016

(86) PCT No.: PCT/JP2016/002589
§ 371 (c)(1),
(2) Date: Feb. 26, 2018

(87) PCT Pub. No.: WO2017/033362
PCT Pub. Date: Mar. 2, 2017

(65) Prior Publication Data
US 2018/0243919 A1    Aug. 30, 2018

(30) Foreign Application Priority Data

Aug. 25, 2015   (JP) .............................. JP2015-165479

(51) Int. Cl.
*A61B 34/37*   (2016.01)
*B25J 9/00*    (2006.01)
(Continued)

(52) U.S. Cl.
CPC .............. *A61B 34/37* (2016.02); *A61B 34/32* (2016.02); *B23P 19/04* (2013.01); *B23Q 15/12* (2013.01);
(Continued)

(58) Field of Classification Search
CPC .... A61B 34/37; A61B 34/32; G05B 19/4182; G05B 2219/40183; B25J 9/0081;
(Continued)

(56) References Cited

U.S. PATENT DOCUMENTS 4,837,734 A * 6/1989 Ichikawa ............. G05B 19/427
                                                              414/1
5,898,599 A * 4/1999 Massie ................... B25J 9/1689
                                                              318/628

(Continued)

FOREIGN PATENT DOCUMENTS

JP      S62-199376 A    9/1987
JP      3217383 B2      10/2001
(Continued)

OTHER PUBLICATIONS

Mitsuishi et al. "Predictive Information Display for Tele-Handling/Machining System." Proceedings of the IEEE/RSJ/GI International Conference on Intelligent Robots and Systems: Advanced Robotic Systems and the Real World, Sep. 12, 1994, pp. 260-267.
(Continued)

*Primary Examiner* — Jaime Figueroa
(74) *Attorney, Agent, or Firm* — Oliff PLC

(57) ABSTRACT

A remote-control manipulator system which includes a manipulator, a slave arm installed in a workspace and configured to perform a series of works comprised of a plurality of processes, a situation information acquisition device configured to acquire situation information indicating a situation of the slave arm, an environment reproducing device configured to reproduce, in a space where the manipulator is installed, environment information relating to an environment in the workspace, and a control device. The control device is configured to cause the environment reproducing device to reproduce the environment information
(Continued)

corresponding to the situation information outputted from the situation information acquisition device.

8 Claims, 8 Drawing Sheets

(51) Int. Cl.

| | |
|---|---|
| B25J 3/00 | (2006.01) |
| G05B 19/418 | (2006.01) |
| B25J 9/16 | (2006.01) |
| B23P 19/04 | (2006.01) |
| B25J 13/00 | (2006.01) |
| B25J 19/04 | (2006.01) |
| B25J 13/08 | (2006.01) |
| B25J 13/06 | (2006.01) |
| B25J 18/00 | (2006.01) |
| B25J 19/02 | (2006.01) |
| B25J 3/04 | (2006.01) |
| B23Q 15/12 | (2006.01) |
| B25J 13/02 | (2006.01) |
| B25J 11/00 | (2006.01) |
| G06F 3/01 | (2006.01) |
| H04N 5/232 | (2006.01) |
| H04N 7/18 | (2006.01) |
| A61B 34/32 | (2016.01) |
| G06T 7/62 | (2017.01) |
| G06T 7/70 | (2017.01) |
| B23P 21/00 | (2006.01) |

(52) U.S. Cl.
CPC . *B25J 3/00* (2013.01); *B25J 3/04* (2013.01); *B25J 9/0081* (2013.01); *B25J 9/0084* (2013.01); *B25J 9/0087* (2013.01); *B25J 9/161* (2013.01); *B25J 9/1602* (2013.01); *B25J 9/163* (2013.01); *B25J 9/1612* (2013.01); *B25J 9/1628* (2013.01); *B25J 9/1633* (2013.01); *B25J 9/1638* (2013.01); *B25J 9/1641* (2013.01); *B25J 9/1646* (2013.01); *B25J 9/1653* (2013.01); *B25J 9/1664* (2013.01); *B25J 9/1669* (2013.01); *B25J 9/1674* (2013.01); *B25J 9/1682* (2013.01); *B25J 9/1689* (2013.01); *B25J 9/1697* (2013.01); *B25J 11/008* (2013.01); *B25J 13/00* (2013.01); *B25J 13/003* (2013.01); *B25J 13/006* (2013.01); *B25J 13/02* (2013.01); *B25J 13/025* (2013.01); *B25J 13/06* (2013.01); *B25J 13/065* (2013.01); *B25J 13/08* (2013.01); *B25J 13/084* (2013.01); *B25J 13/085* (2013.01); *B25J 13/087* (2013.01); *B25J 13/088* (2013.01); *B25J 18/00* (2013.01); *B25J 19/023* (2013.01); *B25J 19/028* (2013.01); *B25J 19/04* (2013.01); *G05B 19/4182* (2013.01); *G06F 3/017* (2013.01); *G06T 7/62* (2017.01); *G06T 7/70* (2017.01); *H04N 5/23219* (2013.01); *H04N 7/181* (2013.01); *B23P 21/00* (2013.01); *B23P 21/002* (2013.01); *G05B 2219/33007* (2013.01); *G05B 2219/35464* (2013.01); *G05B 2219/37297* (2013.01); *G05B 2219/39004* (2013.01); *G05B 2219/39102* (2013.01); *G05B 2219/39439* (2013.01); *G05B 2219/39531* (2013.01); *G05B 2219/39533* (2013.01); *G05B 2219/40022* (2013.01); *G05B 2219/40134* (2013.01); *G05B 2219/40136* (2013.01); *G05B 2219/40139* (2013.01); *G05B 2219/40142* (2013.01); *G05B 2219/40143* (2013.01); *G05B 2219/40145* (2013.01); *G05B 2219/40146* (2013.01); *G05B 2219/40161* (2013.01); *G05B 2219/40162* (2013.01); *G05B 2219/40163* (2013.01); *G05B 2219/40169* (2013.01); *G05B 2219/40182* (2013.01); *G05B 2219/40183* (2013.01); *G05B 2219/40195* (2013.01); *G05B 2219/40387* (2013.01); *G05B 2219/40627* (2013.01); *Y10S 901/02* (2013.01); *Y10S 901/03* (2013.01); *Y10S 901/08* (2013.01); *Y10S 901/09* (2013.01); *Y10S 901/10* (2013.01); *Y10S 901/27* (2013.01); *Y10S 901/41* (2013.01); *Y10S 901/46* (2013.01); *Y10S 901/47* (2013.01)

(58) Field of Classification Search
CPC ...... B25J 9/1602; B25J 9/1612; B25J 13/065; B25J 11/008; B25J 13/02; B25J 9/1628; B25J 9/1633; B25J 19/023; B25J 9/1689; B25J 9/1682; B25J 18/00; B25J 3/00; B25J 9/0087; B25J 9/0084; G06T 7/70; H04N 7/181; H04N 5/23219; G06F 3/017
USPC .................................................. 700/245–264
See application file for complete search history.

(56) References Cited

U.S. PATENT DOCUMENTS

| | | | |
|---|---|---|---|
| 6,016,385 A | 1/2000 | Yee et al. | |
| 6,120,433 A * | 9/2000 | Mizuno | A61B 34/70 600/102 |
| 6,424,885 B1 * | 7/2002 | Niemeyer | A61B 34/70 600/109 |
| 8,718,822 B1 | 5/2014 | Hickman et al. | |
| 9,329,587 B2 * | 5/2016 | Fudaba | G05B 15/02 |
| 9,579,797 B2 * | 2/2017 | Apkarian | B25J 9/1689 |
| 9,622,826 B2 * | 4/2017 | Diolaiti | A61B 34/37 |
| 9,632,573 B2 * | 4/2017 | Ogawa | G06F 3/01 |
| 2005/0267826 A1 | 12/2005 | Levy et al. | |
| 2008/0046122 A1 * | 2/2008 | Manzo | A61B 1/00149 700/245 |
| 2011/0046781 A1 * | 2/2011 | Summer | B25J 9/1689 700/248 |
| 2012/0143353 A1 * | 6/2012 | Kishi | B25J 3/04 700/3 |
| 2012/0191247 A1 * | 7/2012 | Kishi | B25J 3/04 700/264 |
| 2012/0239191 A1 * | 9/2012 | Versteeg | G06N 3/004 700/246 |
| 2012/0328395 A1 * | 12/2012 | Jacobsen | B25J 3/04 414/1 |
| 2013/0204465 A1 * | 8/2013 | Phillips | G05D 1/0274 701/2 |
| 2014/0121834 A1 * | 5/2014 | Ogawa | B25J 3/04 700/257 |
| 2014/0303643 A1 * | 10/2014 | Ha | A61B 34/30 606/130 |
| 2014/0316430 A1 * | 10/2014 | Hourtash | B25J 9/1689 606/130 |
| 2014/0354689 A1 * | 12/2014 | Lee | A61B 1/00045 345/633 |
| 2016/0303739 A1 * | 10/2016 | Apkarian | B25J 3/04 |

FOREIGN PATENT DOCUMENTS

| | | |
|---|---|---|
| JP | 2003-311661 A | 11/2003 |
| JP | 2005-118953 A | 5/2005 |

OTHER PUBLICATIONS

Aug. 2, 2016 International Search Report issued in International Patent Application No. PCT/JP2016/002589.

(56) References Cited

OTHER PUBLICATIONS

Feb. 27, 2018 International Preliminary Report on Patentability issued in International Patent Application No. PCT/JP2016/002589.
Jun. 21, 2017 Office Action issued in Taiwanese Patent Application No. 105127260.

* cited by examiner

REMOTE-CONTROL MANIPULATOR SYSTEM AND METHOD OF OPERATING THE SAME

TECHNICAL FIELD

The present disclosure relates to a remote-control manipulator system and a method of operating the same.

BACKGROUND ART

A master-slave type remote manipulation device which causes operation of a master arm manipulated by an operator to follow operation of a slave arm is known (e.g., see Patent Document 1).

The remote manipulation device disclosed in Patent Document 1 displays an actual image of a work target and a slave hand part and also content of a current work item on a screen of a television monitor. Thus, in manual operation, a control by a human is prompted, an operator is able to understand the content of the operation to be carried out and proceed the operation smoothly.

REFERENCE DOCUMENT OF CONVENTIONAL ART

Patent Document

[Patent Document 1] JP1987-199376A

DESCRIPTION OF THE DISCLOSURE

Problems to be Solved by the Disclosure

However, even with the remote manipulation device disclosed in Patent Document 1, there is still a room for improvement in order for the operator to intuitively grasp the situation of the slave arm.

The present disclosure is for solving the conventional issue and aims to provide a remote-control manipulator system and a method of operating the same, with which a current situation of a slave arm is able to be intuitively grasped and work efficiency is able to be improved.

SUMMARY OF THE DISCLOSURE

In order to solve the conventional issue, a remote-control manipulator system according to one aspect of the present disclosure includes a manipulator configured to receive a manipulating instruction from an operator, a slave arm installed in a workspace and configured to perform a series of works comprised of a plurality of processes, a situation information acquisition device configured to acquire situation information indicating a situation of the slave arm in the workspace, an environment reproducing device configured to reproduce, in a space where the manipulator is installed, environment information relating to an environment in the workspace, and a control device. The control device is configured to cause the environment reproducing device to reproduce the environment information corresponding to the situation information outputted from the situation information acquisition device.

Thus, it is possible to intuitively grasp the situation of the slave arm to be manipulated by displaying the environment information, such as light, smell, sound, image, etc. to the operator (particularly, skilled person). Therefore, it becomes easier to focus on a remote-controlling work, mistakes of operation are reduced, and fatigue of the operator is reduced. Moreover, work efficiency of the remote control is improved.

A method of operating a remote-control manipulator system according to another aspect of the present disclosure is a method of operating a remote-control manipulator system including a manipulator configured to receive a manipulating instruction from an operator, and a slave arm installed in a workspace and configured to perform a series of works comprised of a plurality of processes. The method includes (A) acquiring situation information indicating a situation of the slave arm in the workspace, and (B) causing an environment reproducing device to reproduce environment information corresponding to the situation information acquired in the acquiring (A), in a space where the manipulator is installed.

Thus, it is possible to intuitively grasp the situation of the slave arm to be manipulated by displaying the environment information, such as light, smell, sound, image, etc. to the operator (particularly, skilled person). Therefore, it becomes easier to focus on the remote-controlling work, mistakes of operation are reduced, and fatigue of the operator is reduced. Moreover, work efficiency of the remote control is improved.

Effect of the Disclosure

According to the remote-control manipulator system and the method of operating the same of the present disclosure, it is possible to intuitively grasp the situation of the slave arm to be manipulated.

MODES FOR CARRYING OUT THE DISCLOSURE

Figure 1:
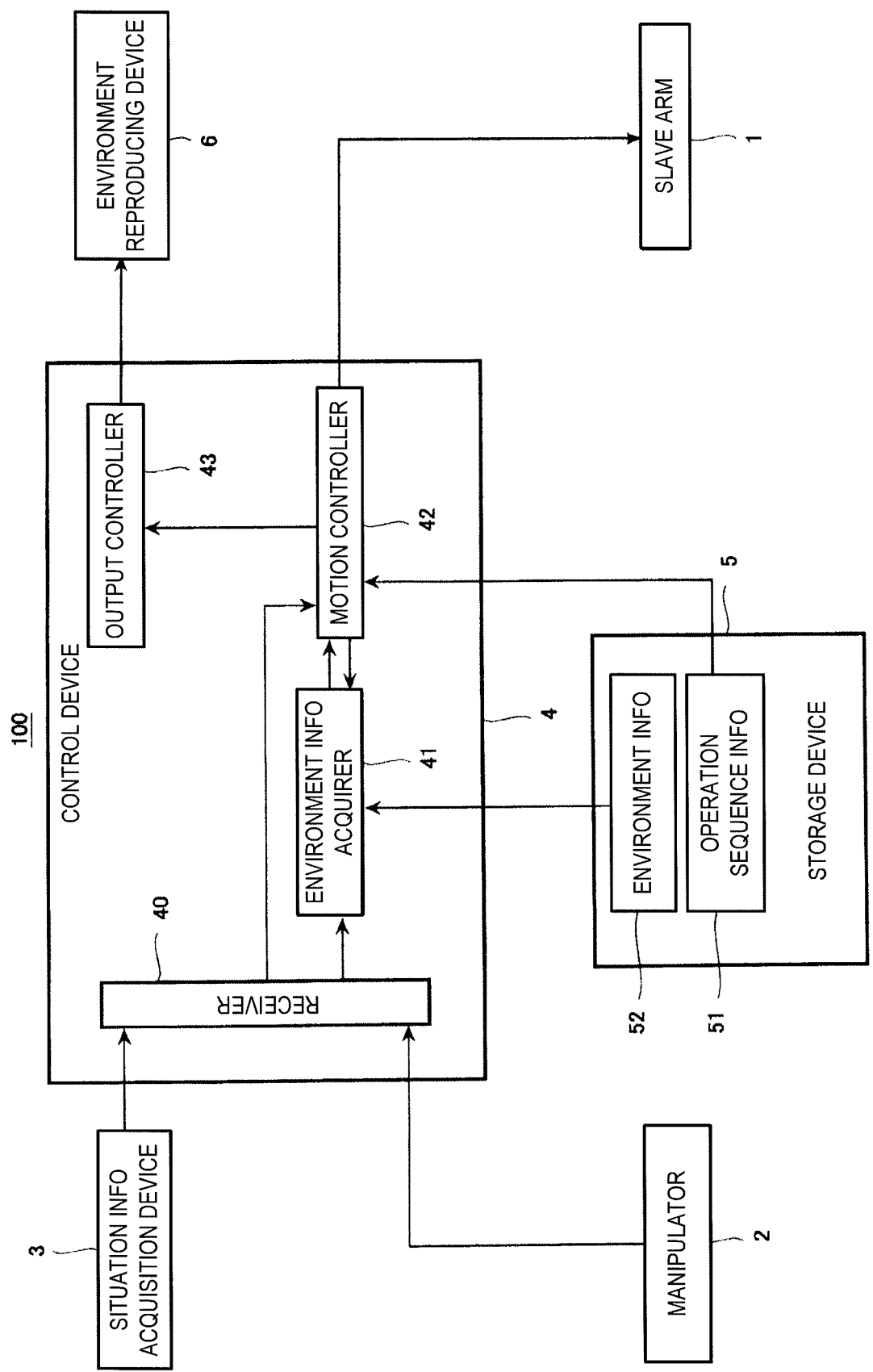
FIG. 1 is a block diagram illustrating a schematic configuration of a remote-control manipulator system according to a first embodiment.

Hereinafter, embodiments of the present disclosure will be described with reference to the drawings. Note that, throughout the drawings, the same reference characters are assigned to the same or corresponding parts and redundant description is omitted. Further, throughout the drawings, elements for describing the present disclosure are selectively illustrated and illustration of the other components may be omitted. Furthermore, the present disclosure is not limited to the following embodiments.

First Embodiment

A remote-control manipulator system according to a first embodiment includes a manipulator which receives a manipulating instruction from an operator, a slave arm which is installed in a workspace and performs a series of works comprised of a plurality of processes, a situation information acquisition device which acquires situation information indicating a situation of the slave arm within the workspace, an environment reproducing device which reproduces, in a space where the manipulator is installed, environment information related to an environment in the workspace, and a control device. The control device is configured to cause the environment reproducing device to reproduce the environment information corresponding to the situation information outputted from the situation information acquisition device.

Moreover, the remote-control manipulator system according to the first embodiment may further include a storage device storing the environment information, and the control device may be configured to acquire, from the storage device, the environment information corresponding to the situation information outputted from the situation information acquisition device.

Further, in the remote-control manipulator system according to the first embodiment, the situation information may be at least one of information in a group comprised of image information in the workspace, information on sound generated in the workspace, information on smell generated in the workspace, information on light generated in the workspace, information on a temperature in the workspace, and information on vibration generated in the workspace.

Furthermore, in the remote-control manipulator system according to the first embodiment, the environment information may be at least one of information in a group comprised of the image information in the workspace, the information on sound generated in the workspace, the information on smell generated in the workspace, illumination information, the information on a temperature in the workspace, the information on vibration generated in the workspace, and information on an operator's posture.

In addition, the remote-control manipulator system according to the first embodiment may be installed with a plurality of slave arms, and the control device may be configured, when operation of the slave arm is switched by the manipulator, to cause the situation information acquisition device to acquire the situation information.

Hereinafter, one example of the remote-control manipulator system according to the first embodiment is described with reference to FIGS. 1 to 3.

[Configuration of Remote-Control Manipulator System]

FIG. 1 is a block diagram illustrating a schematic configuration of the remote-control manipulator system according to the first embodiment.

As illustrated in FIG. 1, the remote-control manipulator system 100 according to the first embodiment includes a slave arm 1, a manipulator 2, a situation information acquisition device 3, a control device 4, a storage device 5, and an environment reproducing device 6, and it is configured so that the slave arm 1 is operated by an operator manipulating the manipulator 2.

The slave arm 1 is a robot which is installed in a workspace and performs a series of works comprised of a plurality of processes. Note that the series of works comprised of the plurality of processes may include works, such as assembling of component(s) to a product and painting.

The slave arm 1 according to the first embodiment is an articulated robot, in a line production or a cell production, which is utilized at a manufacturing plant where products are produced by assembling electric and/or electronic components etc., is disposed along a workbench provided to the manufacturing plant, and is capable of performing at least one of works, such as transferring, assembling or relocating of component(s), and converting the posture, to workpiece (s) on the workbench. Note that the embodiment of the slave arm 1 is not limited to the configuration described above, but may be widely applied to any articulated robots, regardless of a horizontal articulated type or a vertical articulated type.

The manipulator 2 is a device which is installed outside the workspace and receives a manipulating instruction from the operator. The manipulator 2 may be, for example, a master arm, a joystick, or a tablet computer. Note that the manipulator 2 may be separately provided with an input part etc. which inputs a start instruction of a work described later, a notice of completion of the work by a manipulating operation (manual operation), etc. Moreover, the manipulator 2 may be installed in the workspace.

The situation information acquisition device 3 acquires the situation information indicating the situation of the slave arm 1 in the workspace. The situation information is at least one of information in the group comprised of the image information in the workspace, the information on sound generated in the workspace, the information on smell generated in the workspace, the information on light generated in the workspace, the information on the temperature in the workspace, and the information on vibration generated in the workspace.

Specifically, the image information in the workspace is information on the slave arm 1 and its circumference in the workspace captured as an image by a camera etc. More specifically, the image information in the workspace is, for example, information on the position or posture of the slave arm 1 in the workspace, a spatial relationship between the slave arm 1 and a workpiece, or a spatial relationship between the slave arm 1 and an assembled component to which the workpiece is attached, recorded as an image.

Further, the information on sound generated in the workspace, the information on smell generated in the workspace, the information on light generated in the workspace, the information on the temperature in the workspace, and the information on vibration generated in the workspace are information usable in confirming a circumferential situation around the slave arm 1. The information may include sound, smell and light which are generated when the slave arm 1 is welding, and sound which is generated when the slave arm 1 is painting, smell of the paint, color of the paint (light reflected on the paint), etc. The information may also include temperature variation information, such as a rise of the temperature (room temperature) in the workspace due to the slave arm 1 welding or a drop of the temperature in the workspace due to the slave arm 1 cleaning the workpiece, and information on vibration generated when the slave arm 1 attaches the workpiece to the assembled component, etc.

The situation information acquisition device 3 may be, for example, a sensor, an imaging device, a communication device, an encoder, etc. The sensor may be, for example, a laser sensor or a radar sensor etc. for measuring a distance to or a position of the workpiece (assembling component) or the assembled component. Moreover, the sensor may be a stereo camera etc. which is a sensor for measuring a distance from the slave arm 1 to an object in its circumference by using image data obtained from a plurality of imaging devices. In addition, the sensor may be an odor sensor for detecting smell generated in the workspace a microphone for picking up sound, a temperature sensor for detecting the temperature in the workspace, or a pressure sensor (vibration sensor) for detecting vibration of the slave arm 1 or the workpiece.

The communication device may be a communication device for acquiring information from a sensor installed at the workpiece (assembling component), the assembled component, or a given position in the workspace, and information from an imaging device. The encoder may be, for example, an encoder capable of detecting a moved amount or position of the slave arm.

The situation information acquisition device 3 may be disposed to the slave arm 1 itself, or may be disposed at an appropriate position in the workspace. Further, the number of situation information acquisition devices 3 disposed may be one or plural. The attaching position(s) and the attaching number are arbitrary, as long as the suitable number of situation information acquisition devices 3 are disposed at positions where situation information is appropriately acquirable. Further, the situation information acquisition device 3 sequentially acquires the situation information, and the acquired situation information is inputted to the control device 4, which will be described later, and used for controlling the operation of the slave arm 1 in the control device 4.

The storage device 5 is a readable and writable recording medium, which stores operation sequence information 51 and environment information 52 of the remote-control manipulator system 100. Note that, although in the remote-control manipulator system 100 according to the first embodiment, the storage device 5 is provided separately from the control device 4, it may be integrally provided with the control device 4.

The operation sequence information 51 is information related to an operation sequence which defines the series of works to be performed by the slave arm 1 in the workspace, and includes a program for causing the slave arm 1 to perform an automatic operation. Specifically, it is information where an operation order, an operating mode of the slave arm 1 (operating mode), and an operation flow of the operating mode are associated with each other.

The environment information 52 is at least one of information in a group comprised of the image information in the workspace, the information on sound generated in the workspace, the information on smell generated in the workspace, the information on light generated in the workspace, the information on the temperature in the workspace, the information on vibration generated in the workspace, and the information on the operator's posture.

Specifically, the image information in the workspace is information on the slave arm 1 and its circumference in the workspace captured as an image by the camera etc. and stored in the storage device 5. More specifically, the image information in the workspace is, for example, information on the position or posture of the slave arm 1 in the workspace, a spatial relationship between the slave arm 1 and the workpiece, or a spatial relationship between the slave arm 1 and the assembled component to which the workpiece is attached, recorded as an image.

Further, the information on sound generated in the workspace, the information on smell generated in the workspace and the information on light generated in the workspace are information usable in confirming the circumference situation around the slave arm 1. The information may include sound, smell and light which are generated when the slave arm 1 performs welding, and sound which is generated when the slave arm 1 is painting, smell of the paint, color of the paint (light reflected on the paint), etc., and these information is stored in the storage device 5.

Further, the information on the temperature in the workspace, the information on vibration generated in the workspace, and the information on the operator's posture are information usable in confirming the circumference situation around the slave arm 1. The information may include temperature variation information, such as a rise of the temperature (room temperature) in the workspace due to the slave arm 1 welding or a drop of the temperature in the workspace due to the slave arm 1 cleaning the workpiece, and information on vibration generated when the slave arm 1 attaches the workpiece to the assembled component. Moreover, the information may include information on posture which was taken by the operator when the operator manually performed the work currently executed by the slave arm 1. Moreover, these information is stored in the storage device 5.

The control device 4 controls the operation of the slave arm 1, and includes a receiver 40, an environment information acquirer 41, a motion controller 42, and an output controller 43, as functional blocks. The control device 4 may be comprised of, for example, an arithmetic part (not illustrated), such as a microcontroller, an MPU and a PLC (Programmable Logic Controller), a logic circuit, etc., and a memory part (not illustrated), such as a ROM or a RAM. Moreover, each functional block provided to the control device 4 is implementable by the arithmetic part of the control device 4 reading and executing the program stored in the memory part or the storage device 5.

Note that the control device 4 may not only be in a form comprised of a single control device, but also in a form comprised of a group of control devices in which a plurality of control devices collaborate with each other to execute the control of the slave arm 1 (remote-control manipulator system 100).

The receiver 40 receives an input signal transmitted from the outside of the control device 4. The input signal received by the receiver 40 may be, for example, a signal transmitted from the manipulator 2, a signal transmitted from a manipulating instruction part (not illustrated) other than the manipulator 2, or a signal indicating the situation information transmitted from the situation information acquisition device 3, etc.

The environment information acquirer 41 acquires, from the environment information 52 stored in the storage device 5, environment information corresponding to the situation information received by the receiver 40 from the situation information acquisition device 3, and outputs the environment information to the motion controller 42. The environment information corresponding to the situation information received from the situation information acquisition device 3 may be, for example, when the slave arm 1 is painting, a pre-captured image in the workspace, a pre-created image, such as an animation, a pre-recorded spray sound, the smell of the paint used for painting, or the color of the paint.

When the receiver 40 receives a manipulating instruction from the manipulator 2 as the input signal, the motion controller 42 determines the operating mode of the process which the slave arm 1 carries out in the series of works by using the manipulating instruction as a trigger. The motion controller 42 is capable of performing the determination of the operating mode of the process which the slave arm 1 carries out next, with reference to the operation sequence information 51 stored in the storage device 5. Once the motion controller 42 determines the operating mode, it controls the slave arm 1 so that the slave arm 1 is operated in the determined operating mode.

If the motion controller 42 determines that the slave arm 1 is to be automatically operated, it reads the operation sequence information 51, and controls the slave arm 1 to perform the operation defined by the program contained in the operation sequence information 51.

On the other hand, if the motion controller 42 determines that the slave arm 1 is to be manipulated to operate, it controls the slave arm 1 to perform the operation based on the manipulating instruction received from the manipulator 2 by the receiver 40. Note that, when the slave arm 1 is to be automatically operated, once the automatic operation of the slave arm 1 is ended, the motion controller 42 transmits information indicating that the automatic operation is ended to the output controller 43.

Further, in at least one of the plurality of processes when starting one of the automatic operation and the manipulating operation, during the automatic operation, when one of the automatic operation and the manipulating operation is ended, or when an acquiring instruction for the situation information is inputted from an instruction acquisition device 7 described later, the motion controller 42 outputs the environment information 52 outputted from the environment information acquirer 41 to the output controller 43. Note that in each process, the motion controller 42 may output the environment information 52 to the output controller 43 when starting one of the automatic operation and the manipulating operation, during the automatic operation, or when one of the automatic operation and the manipulating operation is ended. Further, the motion controller 42 may acquire, instead of the environment information 52 which is outputted from the environment information acquirer 41, the situation information outputted from the situation information acquisition device 3 via the receiver 40, and output the situation information to the output controller 43 as the environment information.

The output controller 43 controls the environment reproducing device 6 to output information to be notified to the operator etc. For example, when the output controller 43 receives the information indicating the start of the automatic operation from the motion controller 42, or the information indicating the start of the manipulating operation from the manipulator 2 via the motion controller 42 and the receiver 40, it may control the environment reproducing device 6 to output this information and, additionally, the environment information 52 or the situation information. Further, the output controller 43 may control the environment reproducing device 6 to output the environment information 52 or the situation information while the motion controller 42 is executing the automatic operation. Furthermore, when the output controller 43 receives the information indicating the end of the automatic operation from the motion controller 42, or the output controller 43 receives the information indicating the end of the manipulating operation from the manipulator 2 via the motion controller 42 and the receiver 40, it may control the environment reproducing device 6 to output this information and additionally, the environment information 52 or the situation information.

The environment reproducing device 6 is provided at a position where the operator of the manipulator 2 is able to sense the outputted information (outside the workspace; the space where the manipulator 2 is installed), and outputs the information transmitted from the control device 4. Further, the environment reproducing device 6 outputs the notification of the end of the automatic operation of the slave arm 1 by displaying, expressing with sound or light, etc.

Here, a specific example of the environment reproducing device 6 will be described in detail with reference to FIG. 2.

Figure 2:
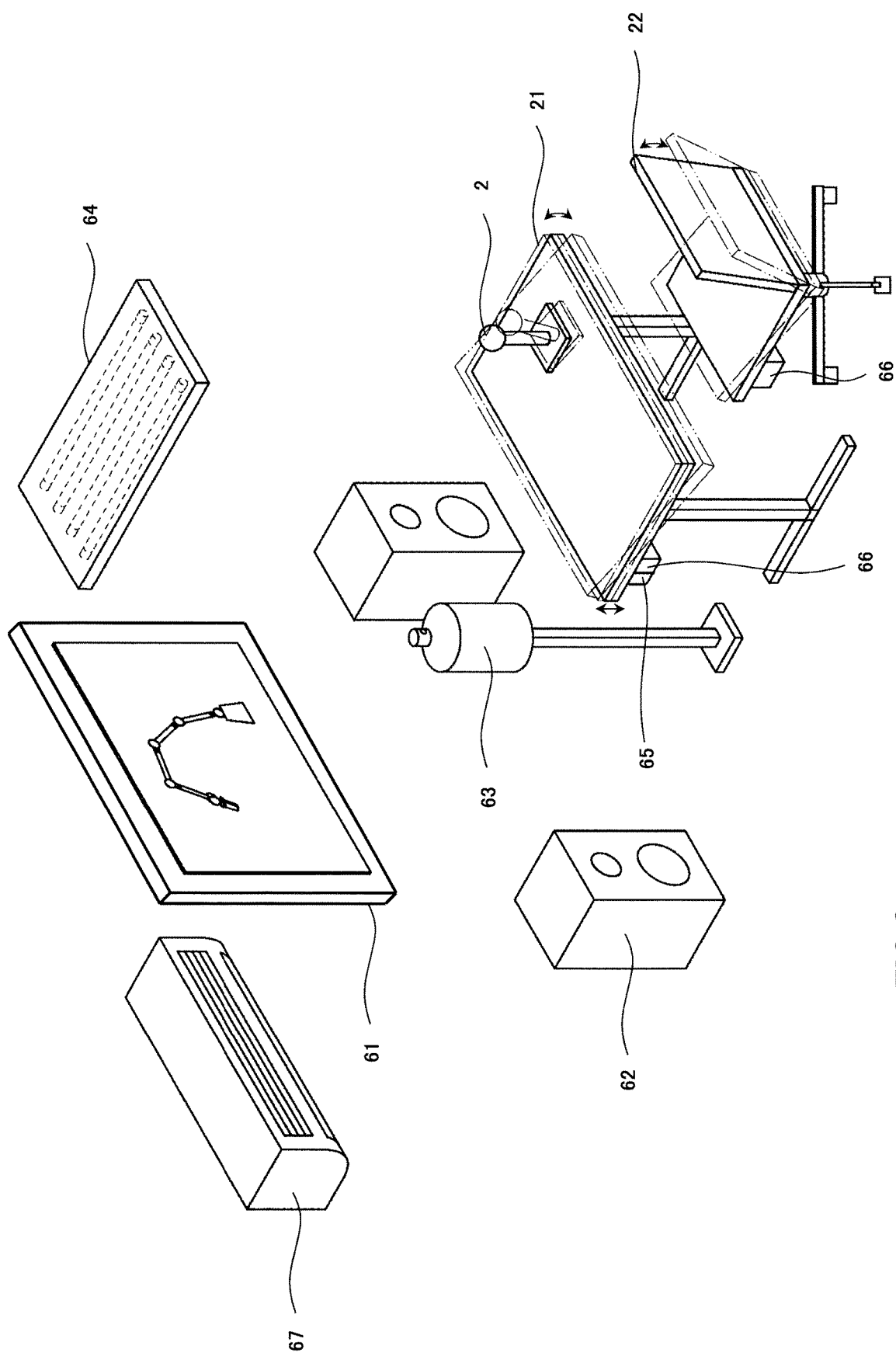
FIG. 2 is a schematic diagram illustrating a specific example of an environment reproducing device of the remote manipulator system illustrated in FIG. 1.

FIG. 2 is a schematic diagram illustrating the specific example of the environment reproducing device of the remote manipulator system illustrated in FIG. 1.

As illustrated in FIG. 2, the environment reproducing device 6 may include a display device 61, such as a monitor, a speaker 62, a spray can 63, a lighting device 64, a desk 21, a chair 22, a vibration device 65 which vibrates the manipulator 2, a posture changing device 66 which changes (tilts) postures of the desk 21, the chair 22, or the manipulator 2, an air conditioner 67, etc. When the environment reproducing device 6 is constituted by the display device 61, it displays the information transmitted from the control device 4 as an image, for example, letter(s), a painting, a picture, a video, etc. When the environment reproducing device 6 is constituted by the speaker 62, it outputs the information transmitted from the control device 4 as a sound.

Further, when the environment reproducing device 6 is constituted by the spray can 63, an odor component is filled in a container in advance, and the information transmitted from the control device 4 is outputted as smell. Specifically, for example, when the slave arm 1 is painting, the odor component of the paint used for the painting may be filled in the container, and then the spray can 63 may release the odor component once the environment information is outputted from the control device 4.

Further, when the environment reproducing device 6 is constituted by the lighting device 64, it reproduces the situation of the slave arm 1 by outputting the information transmitted from the control device 4 as light. Specifically, for example, when the slave arm 1 is welding, the lighting device 64 may output (radiate) the color of the light generated in welding, and may output the light so that it blinks. Further, when the slave arm 1 is painting, the lighting device 64 may output the color of the paint. Furthermore, the color to be outputted for the process currently executed by the slave arm 1 may be decided in advance and the lighting device 64 may output the color.

Further, when the environment reproducing device 6 is constituted by the vibration device 65, it outputs the information transmitted from the control device 4 as vibration. Specifically, for example, the vibration device 65 vibrates the manipulator 2 which the operator is currently manipulating, the desk 21 on which the manipulator 2 is disposed, or the chair 22 on which the operator is sitting.

Further, when the environment reproducing device 6 is constituted by the posture changing device 66, it outputs the information transmitted from the control device 4 as posture information. Specifically, for example, the posture changing device 6 tilts a top plate of the desk 21 on which the manipulator 2 is disposed or the chair 22 on which the operator is sitting. Thus, the operator takes the posture which the operator takes when manually executing the process currently executed by the slave arm 1, and the operator is able to grasp the process currently executed by the slave arm 1.

Furthermore, when the environment reproducing device 6 is constituted by the air conditioner 67, it outputs the information transmitted from the control device 4 as a temperature. Specifically, the air conditioner 67 adjusts the temperature in the space where the manipulator 2 is disposed. For example, when the slave arm 1 is welding, the air conditioner 67 is operated to raise the temperature in the space where the manipulator 2 is disposed.

[Operation and Effect of Remote-Control Manipulator System]

Next, operation and effect of the remote-control manipulator system 100 according to the first embodiment are described with reference to FIGS. 1 to 3. Note that since the operation of performing the series of works by the operator manipulating the manipulator 2 to operate the slave arm 1 is executed similar to a known remote-control manipulator system, detailed description thereof is omitted. Moreover, the following operation is executed by the arithmetic part of the control device 4 reading the program stored in the memory part or the storage device 5.

Figure 3:
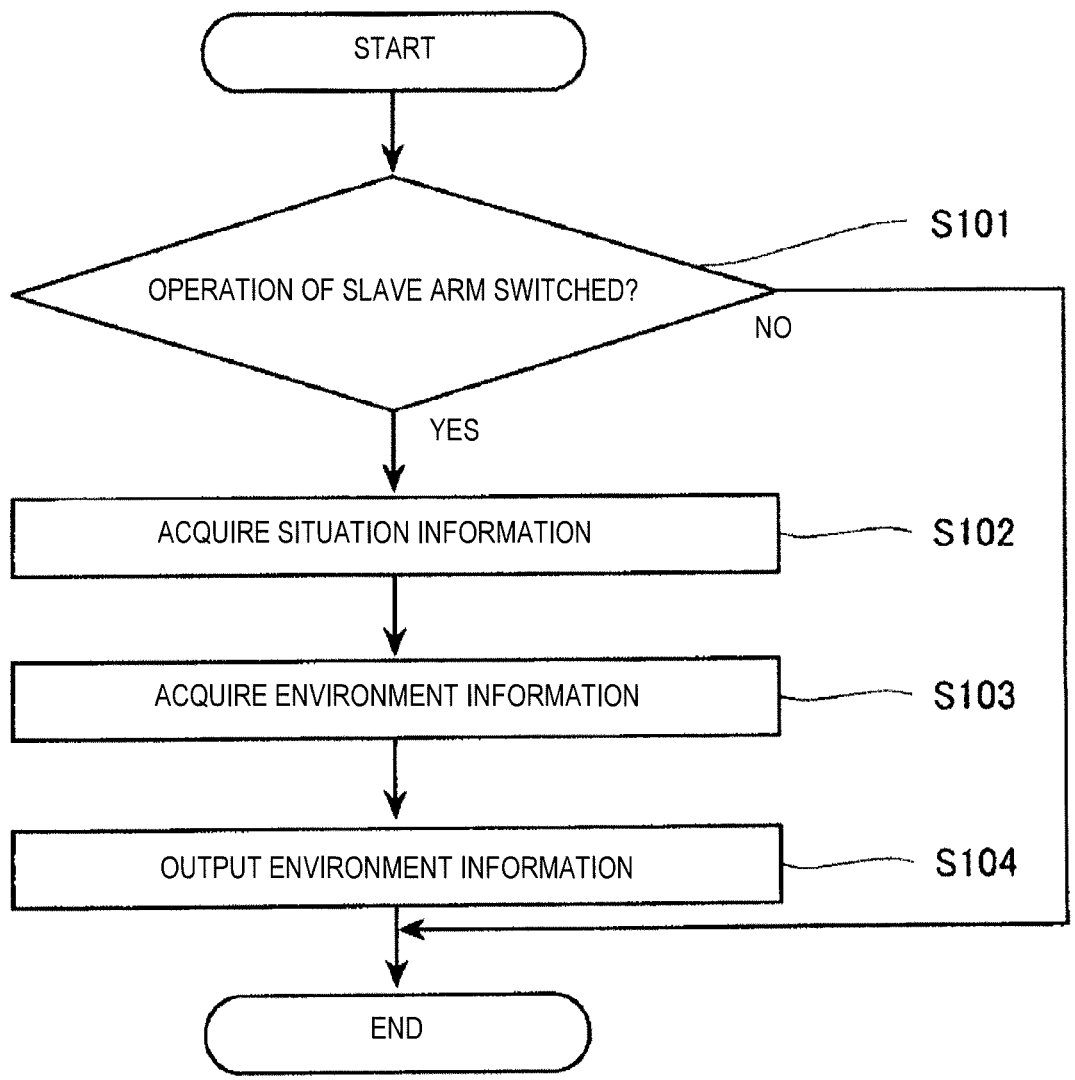
FIG. 3 is a flowchart illustrating operation of the remote-control manipulator system according to the first embodiment.

FIG. 3 is a flowchart illustrating operation of the remote-control manipulator system 100 according to the first embodiment.

As illustrated in FIG. 3, the control device 4 determines whether the operator has switched the operation of the slave arm 1 (Step S101).

Specifically, the motion controller 42 of the control device 4 determines whether the information indicating that the operation is switched from a certain slave arm 1 to another slave arm 1 or information indicating that the slave arm 1 in the automatic operation is switched to be in the manipulating operation, that is, information on a manipulation start instruction for a given slave arm 1, is inputted from the manipulator 2 via the receiver 40.

If the motion controller 42 of the control device 4 determines that the information on the manipulation start instruction is not inputted (NO at Step S101), it ends this program. Note that, when the control device 4 ends this program, it again executes this program, for example, after 50 msec. On the other hand, if the motion controller 42 of the control device 4 determines that the information on the manipulation start instruction is inputted (YES at Step S101), it executes processing illustrated at Step S102.

At Step S102, the control device 4 acquires the situation information acquired by the situation information acquisition device 3. Specifically, for the given slave arm 1, the receiver 40 receives the situation information acquired by the situation information acquisition device 3, and the motion controller 42 acquires the received situation information. Note that, the motion controller 42 may acquire, when the given slave arm 1 is automatically operated, the information on the process currently executed by the given slave arm 1 or, when the given slave arm 1 is in a manipulating instruction input standby state (manipulation standby state), the information on the process executed immediately previously, as the situation information from the motion controller 42. In this case, the motion controller 42 constitutes the situation information acquisition device.

Next, the control device 4 acquires the environment information corresponding to the situation information acquired at Step S102 from the environment information 52 in the storage device 5 (Step S103). Specifically, the motion controller 42 of the control device 4 outputs the situation information acquired at Step S102 to the environment information acquirer 41.

The environment information acquirer 41 acquires the environment information 52 from the storage device 5, selects the environment information corresponding to the inputted situation information from the environment information 52 in the storage device 5, and outputs it to the motion controller 42.

Next, the control device 4 outputs the environment information acquired at Step S103 to the environment reproducing device 6 (Step S104). Specifically, the motion controller 42 of the control device 4 outputs the environment information acquired at Step S103 to the environment reproducing device 6 via the output controller 43.

Thus, the environment reproducing device 6 is capable of reproducing the environment information corresponding to the situation of the given slave arm 1 and notifying it to the operator. Specifically, for example, when the slave arm 1 is executing the painting process or the painting process is ended, the environment reproducing device 6 may output the image of the slave arm 1 painting, output the spray sound generated when painting, or output (emit) from the lighting device the color of the paint used for the painting. Further, for example, when the slave arm 1 is executing the painting process or the painting process is ended, the environment reproducing device 6 may vibrate the manipulator 2 etc., tilt the chair 22 etc. which is currently used by the operator, or raise the temperature in the space where the manipulator 2 is disposed.

Here, when the situation information acquired by the situation information acquisition device 3 is image information, the environment reproducing device 6 may reproduce the image information stored in the storage device 5 as the environment information, reproduce information other than the image information (e.g., sound information), or reproduce the image information and the information other than the image information.

In the remote-control manipulator system 100 according to the first embodiment configured as described above, when the operator manipulates the manipulator 2 to switch the operation of the slave arm 1, the environment reproducing device 6 reproduces the environment information corresponding to the situation of the given slave arm 1 which is switched. Thus, the operator can grasp the situation of the slave arm 1 intuitively and with realistic sensation. Therefore, the operator can easily call up the process which the slave arm 1 executes next.

Further, since the situation of the slave arm 1 can be grasped even if the slave arm 1 of which operation is switched is in the automatic operation, it is possible to provide a remote-control manipulator system with excellent usability.

Particularly, when the operator is a skilled worker, by the environment reproducing device 6 reproducing the environment information corresponding to the situation of the given slave arm 1, the process which the slave arm 1 executes next is easily called up.

Therefore, in the remote-control manipulator system 100 according to the first embodiment, the operator becomes easier to focus on the remote-controlling work, mistakes of operation are reduced, and fatigue of the operator is reduced. Moreover, the work efficiency of the remote control is improved.

Note that in the first embodiment, although a form in which the control device 4 selects the environment information corresponding to the situation information on the slave arm 1 from the environment information 52 stored in the storage device 5 and the environment reproducing device 6 reproduces it, is adopted, it is not limited to this. For example, when the operator manipulates, while the slave arm 1 is in the automatic operation, the manipulator 2 to switch the operation so that the slave arm 1 is manipulated, or when the slave arm 1 is performing the automatic operation, a form in which the situation information acquired by the situation information acquisition device 3 may be outputted as the environment information and the environment reproducing device 6 directly reproduces it in real time may be adopted.

Second Embodiment

A remote-control manipulator system according to the second embodiment is configured so that, in the remote-control manipulator system according to the first embodiment, an instruction acquisition device which receives an acquiring instruction for the situation information from the operator and outputs the acquiring instruction to the control device is further provided, and the control device causes the situation information acquisition device to acquire the situation information upon receiving the acquiring instruction from the instruction acquisition device.

Hereinafter, one example of the remote-control manipulator system according to the second embodiment is described in detail with reference to FIGS. 4 and 5.

[Configuration of Remote-Control Manipulator System]

Figure 4:
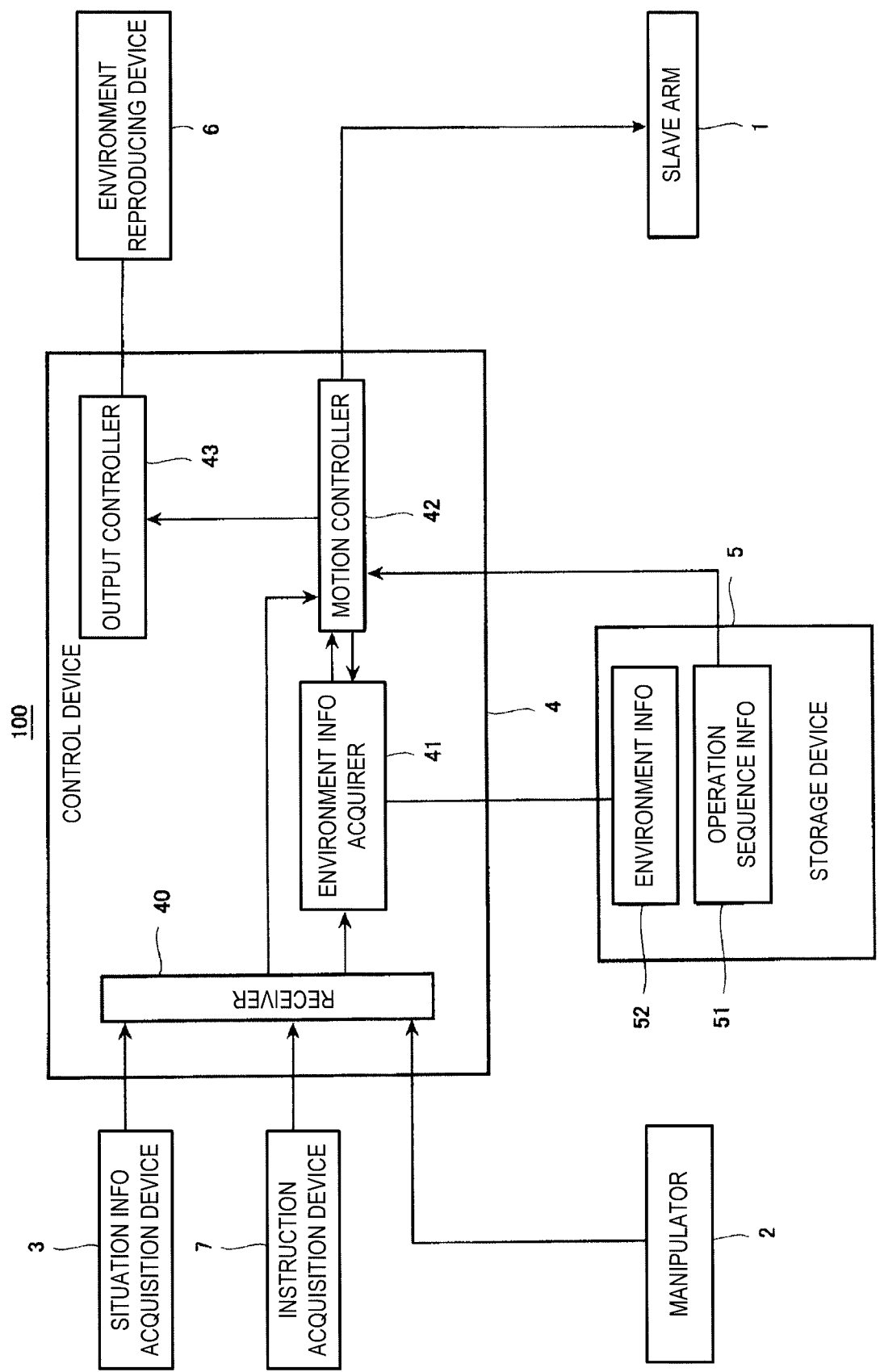
FIG. 4 is a block diagram illustrating a schematic configuration of a remote-control manipulator system according to a second embodiment.

FIG. 4 is a block diagram illustrating a schematic configuration of the remote-control manipulator system according to the second embodiment.

As illustrated in FIG. 4, the remote-control manipulator system 100 according to the second embodiment has the same basic configuration to the remote-control manipulator system 100 according to the first embodiment, but it is different in that an instruction acquisition device 7 is further provided.

The instruction acquisition device 7 is disposed outside the workspace and configured to receive an acquiring instruction for acquiring the situation of a given slave arm 1 from the operator and output the acquiring instruction to the control device 4. For example, when a plurality of slave arms 1 are disposed in the workspace, the instruction acquisition device 7 may be configured to output an acquiring instruction for each slave arm 1, or may be configured to output an acquiring instruction for an arbitrary slave arm 1.

Note that the instruction acquisition device 7 may be disposed in the workspace. Further, the instruction acquisition device 7 may be disposed separately from the manipulator 2 or formed integrally with the manipulator 2.

[Operation and Effect of Remote-Control Manipulator System]

Next, operation and effect of the remote-control manipulator system 100 according to the second embodiment are described with reference to FIGS. 4 and 5. Note that, the following operation is executed by the arithmetic part of the control device 4 reading the program stored in the memory part or the storage device 5.

Figure 5:
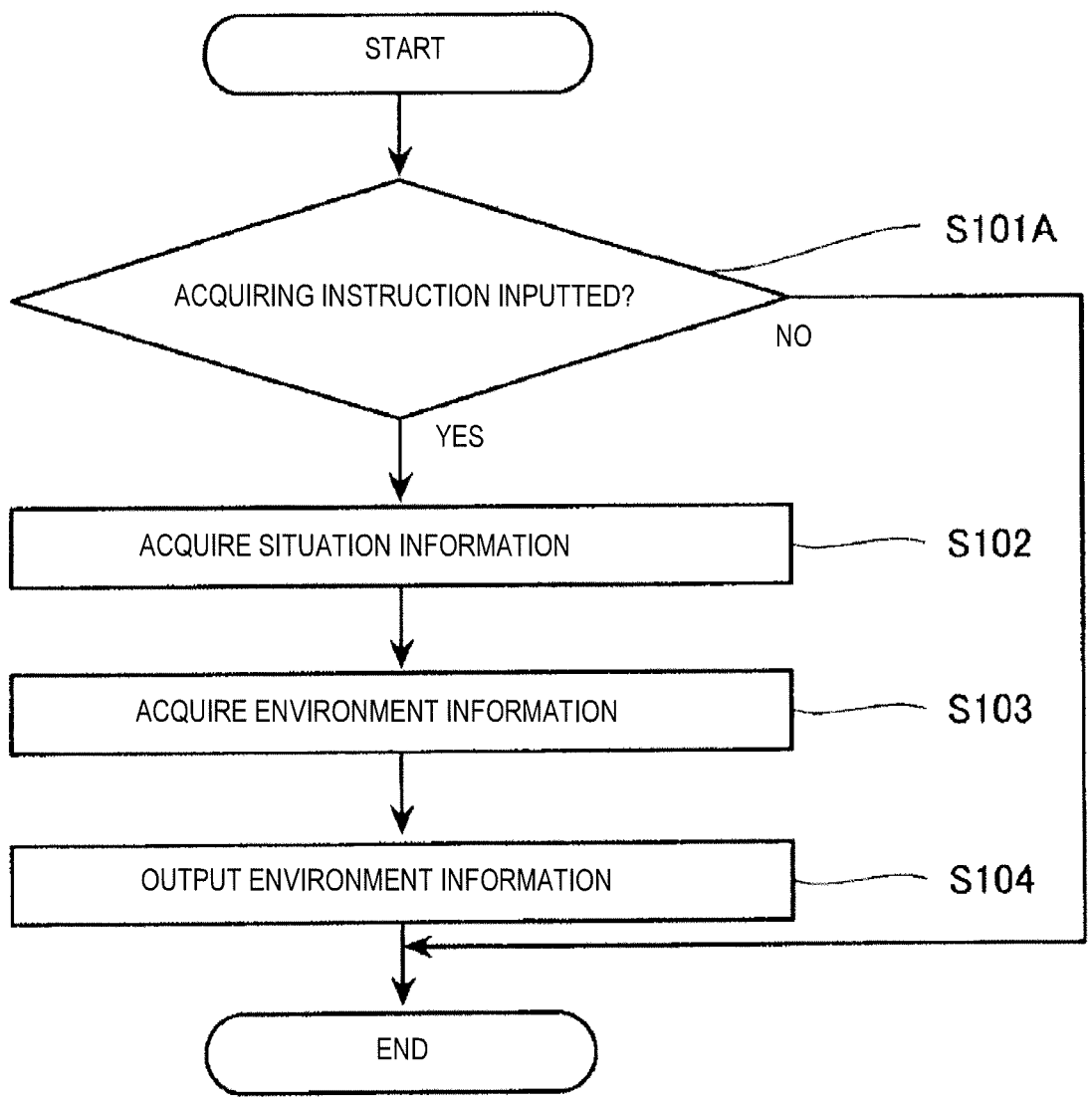
FIG. 5 is a flowchart illustrating operation of the remote-control manipulator system according to the second embodiment.

FIG. 5 is a flowchart illustrating operation of the remote-control manipulator system according to the second embodiment.

As illustrated in FIG. 5, although the operation of the remote-control manipulator system 100 according to the second embodiment is basically the same as the operation of the remote-control manipulator system 100 according to the first embodiment, it is different in that Step S101A is executed instead Step S101.

Specifically, the control device 4 determines whether the acquiring instruction is inputted from the instruction acquisition device 7 (Step S101A). More specifically, the motion controller 42 of the control device 4 determines whether the acquiring instruction is inputted for the given slave arm 1 from the instruction acquisition device 7 via the receiver 40.

Here, the case where it is determined that the acquiring instruction is inputted means a case where that the instruction acquisition device 7 receives an acquiring instruction for acquiring the situation of the given slave arm 1 from the operator, and the instruction acquisition device 7 outputs the acquiring instruction to the receiver 40 of the control device 4 and the motion controller 42 acquires the acquiring instruction via the receiver 40.

If the motion controller 42 of the control device 4 determines that the acquiring instruction is not inputted (NO at Step S101A), it ends this program. Note that, when the control device 4 ends this program, it again executes this program, for example, after 50 msec.

On the other hand, if the motion controller 42 of the control device 4 determines that the acquiring instruction is inputted (YES at Step S101A), it executes processing illustrated at Step S102. Hereinafter, the operation similar to that of the remote-control manipulator system 100 according to the first embodiment is executed.

In the remote-control manipulator system 100 according to the second embodiment configured as described above, the operator manipulates the instruction acquisition device 7, so that the environment reproducing device 6 reproduces the environment information corresponding to the situation of the given slave arm 1. Thus, the operator can grasp the situation of the slave arm 1 intuitively and with realistic sensation. Therefore, the operator can easily call up the process which the slave arm 1 executes next.

For example, in a case where a plurality of slave arms 1 are disposed in the workspace, when the operator causes the manipulator 2 to execute the manipulation on the given slave arm 1, by the environment reproducing device 6 reproducing the environment information corresponding to the situation of the slave arm 1, it is possible to easily grasp the situation of the slave arm 1.

Further, even in a case where a single slave arm 1 is disposed in the workspace, when the operator is working away from the manipulator 2 and, upon ending the automatic operation of a certain process of the slave arm 1, the next process is started, by the environment reproducing device 6 reproducing the environment information corresponding to the situation of the slave arm 1, it is possible to easily grasp the situation of the slave arm 1.

Note that in the second embodiment, although a form in which the environment information corresponding to the situation information on the slave arm 1 is selected from the environment information 52 stored in the storage device 5 and the environment reproducing device 6 reproduces it, is adopted, it is not limited to this. For example, a form in which, when the operator instructs the acquisition of the situation information on the slave arm 1 while the slave arm 1 is in the automatic operation, the environment reproducing device 6 directly reproduces the situation information on the slave arm 1 in real time, may be adopted.

Third Embodiment

A remote-control manipulator system according to a third embodiment is configured so that in the remote-control manipulator system according to the first or second embodiment, the control device causes, when at least one process out of a plurality of processes is to be started or once at least one process is ended, the situation information acquisition device to acquire the situation information.

Hereinafter, one example of the remote-control manipulator system according to the third embodiment is described with reference to FIG. 6. Note that, since the remote-control manipulator system 100 according to the third embodiment has a similar configuration to the remote-control manipulator system 100 according to the first embodiment, detailed description of the configuration thereof is omitted.

[Operation and Effect of Remote-Control Manipulator System]

Figure 6:
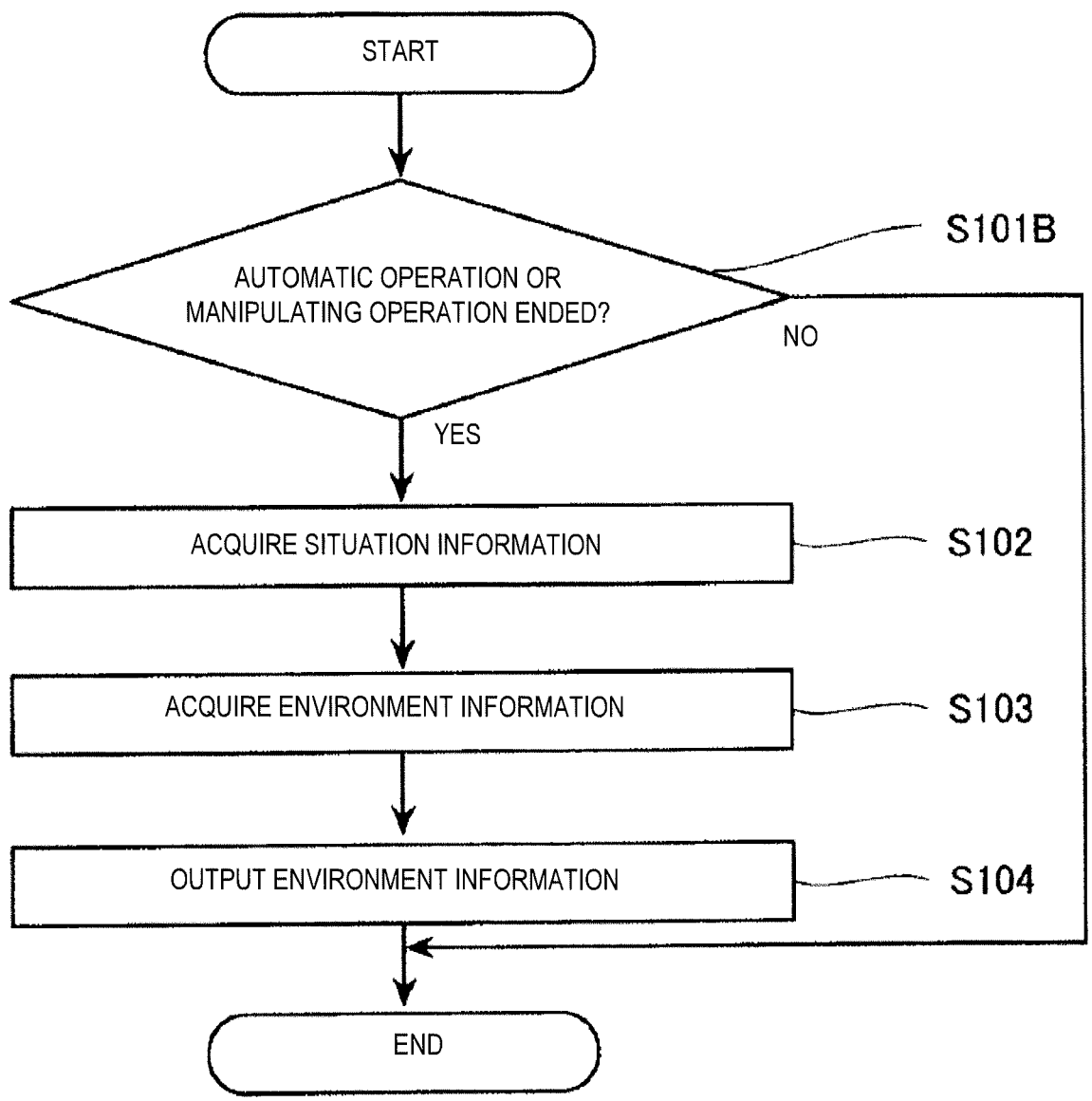
FIG. 6 is a flowchart illustrating operation of a remote-control manipulator system according to a third embodiment.

FIG. 6 is a flowchart illustrating operation of the remote-control manipulator system according to the third embodiment. Note that, the following operation is executed by the arithmetic part of the control device 4 reading the program stored in the memory part or the storage device 5.

As illustrated in FIG. 6, although the operation of the remote-control manipulator system 100 according to the third embodiment is basically the same as the operation of the remote-control manipulator system 100 according to the first embodiment, it is different in that Step S101B is executed instead of Step S101.

Specifically, the control device 4 determines whether the automatic operation or the manipulating operation of a certain process for a given slave arm 1 is ended (Step S101B). More specifically, the motion controller 42 of the control device 4 determines whether the automatic operation of the given slave arm 1 is ended, or whether the end information on the manipulating operation of the given slave arm 1 is received via the receiver 40 by the operator manipulating the manipulator 2 etc.

Note that when a plurality of slave arms 1 are disposed in the workspace, which slave arm 1 the situation information is to be acquired for may be determined by the operator manipulating the manipulator 2 etc., or may suitably be determined by the control device 4.

If the motion controller 42 of the control device 4 determines that the automatic operation or the manipulating operation of the given slave arm 1 is not ended (NO at Step S101B), it ends this program. Note that, when the control device 4 ends this program, it again executes this program, for example, after 50 msec. On the other hand, if the motion controller 42 of the control device 4 determines that the automatic operation or the manipulating operation of the given slave arm 1 is ended (YES at Step S101B), it executes processing illustrated at Step S102. Hereinafter, the operation similar to that of the remote-control manipulator system 100 according to the first embodiment is executed.

Even with the remote-control manipulator system 100 according to the third embodiment configured as above, similar operations and effects to those of the remote-control manipulator system 100 according to the first embodiment are obtained.

Note that in the third embodiment, a form in which, at Step S101B, the control device 4 determines whether the automatic operation or the manipulating operation of a certain process is ended is adopted, but it is not limited to this. For example, a form in which the control device 4 determines whether to start the automatic operation or the manipulating operation in a certain process, or a form in which the control device 4 determines whether it is a given time or whether a given period of time has elapsed may be adopted.

Fourth Embodiment

A remote-control manipulator system according to a fourth embodiment is configured so that in the remote-control manipulator system according to one of the first to third embodiments, a storage device storing work information relating to each process which the slave arm carries out is further provided, and the control device identifies the process currently executed by the slave arm and causes the environment reproducing device to reproduce, as the environment information, work information on the process subsequent to the identified process outside the workspace.

Furthermore, in the remote-control manipulator system according to the fourth embodiment, the work information may be at least one of information in a group comprised of image information in the workspace, information on sound generated in the workspace, information on smell generated in the workspace, illumination information, information on a temperature in the workspace, information on vibration generated in the workspace, and information on an operator's posture.

Hereinafter, one example of the remote-control manipulator system according to the fourth embodiment is described with reference to FIGS. 7 and 8.

[Configuration of Remote-Control Manipulator System]

Figure 7:
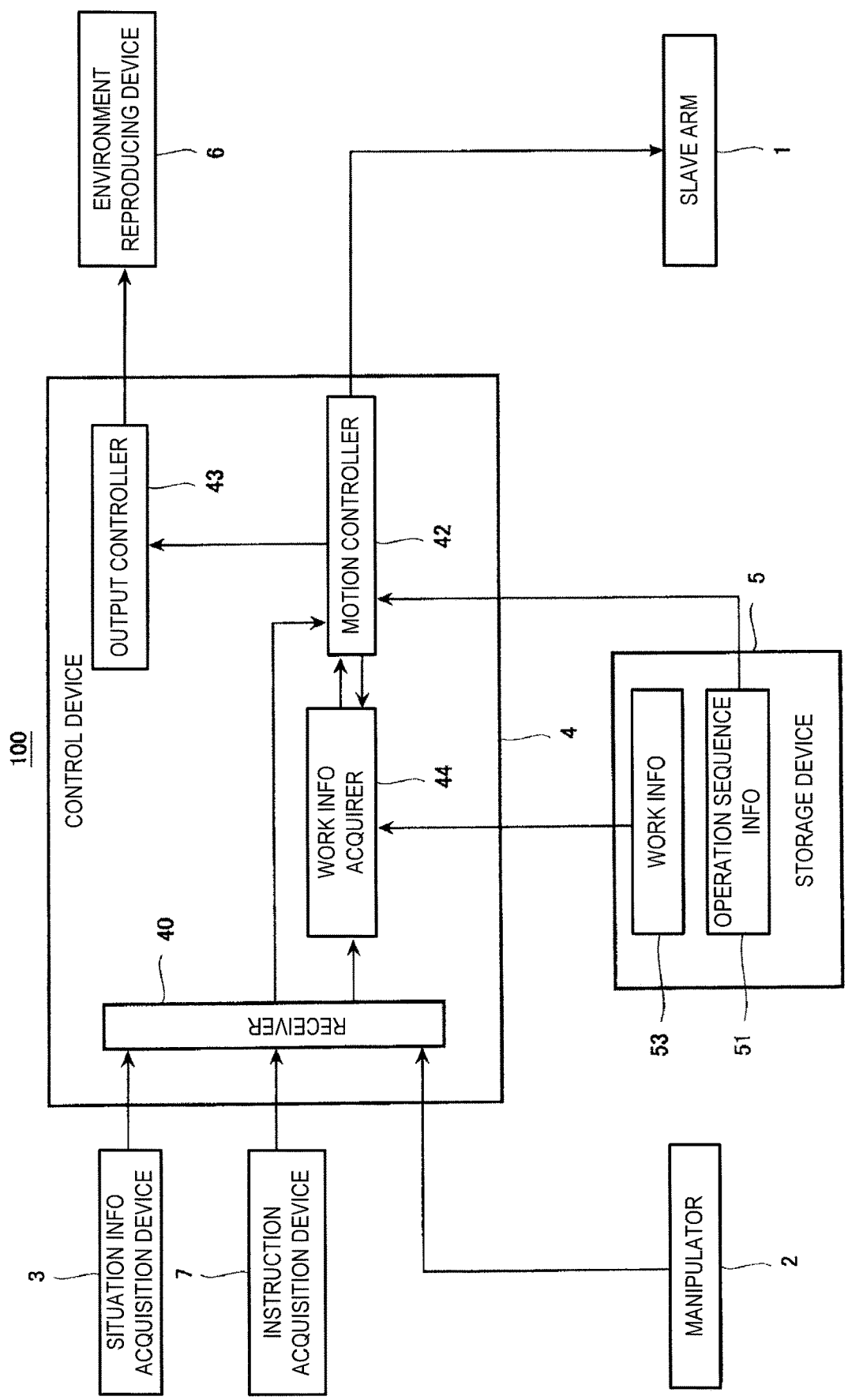
FIG. 7 is a block diagram illustrating a schematic configuration of a remote-control manipulator system according to a fourth embodiment.

FIG. 7 is a block diagram illustrating a schematic configuration of the remote-control manipulator system according to the fourth embodiment.

As illustrated in FIG. 7, the remote-control manipulator system 100 according to the fourth embodiment has the same basic configuration to the remote-control manipulator system 100 according to the first embodiment, but it is different in that a work information acquirer 44 is formed in the control device 4 and work information 53 is stored in the storage device 5.

The work information acquirer 44 acquires the process information currently executed by the given slave arm 1 from the motion controller 42, and identifies the process. Further, the work information acquirer 44 acquires the work information on the process subsequent to the identified process from the work information 53 stored in the storage device 5, and outputs the work information to the motion controller 42 as the environment information.

Note that the work information 53 is at least one of information in a group comprised of the image information in the workspace, the information on sound generated in the workspace, the information on smell generated in the workspace, the information on light generated in the workspace, the information on the temperature in the workspace, the information on vibration generated in the workspace, and the information on the operator's posture.

Specifically, the image information in the workspace is information on the slave arm 1 and its circumference in the workspace captured as an image by the camera etc. and stored in the storage device 5. More specifically, the image information in the workspace is, for example, information on the position or posture of the slave arm 1 in the workspace, a spatial relationship between the slave arm 1 and the workpiece, or a spatial relationship between the slave arm 1 and the assembled component to which the workpiece is attached, recorded as an image. Further, the image information in the workspace may be, for example, a pre-captured image in the workspace or a pre-created image, such as an animation etc.

Further, the information on sound generated in the workspace, the information on smell generated in the workspace and the information on light generated in the workspace are information usable in confirming the circumference situation around the slave arm 1. The information may include sound, smell and light which are generated when the slave arm 1 is welding, sound which is generated when the slave arm 1 is painting, smell of the paint, color of the paint (light reflected on the paint), etc., and these information is stored in the storage device 5.

Further, the information on the temperature in the workspace, the information on vibration generated in the workspace, and the information on the operator's posture are information usable in confirming the circumference situation around the slave arm 1. The information may also include temperature variation information, such as a rise of the temperature (room temperature) in the workspace due to the slave arm 1 welding or a drop of the temperature in the workspace due to the slave arm 1 cleaning the workpiece, and information on vibration generated when the slave arm 1 attaches the workpiece to the assembled component. Further, the information may include information on a posture which the operator takes when manually executing the process currently executed by the slave arm 1. Moreover, these information is stored in the storage device 5.

[Operation and Effect of Remote-Control Manipulator System]

Next, operation and effect of the remote-control manipulator system 100 according to the fourth embodiment are described with reference to FIGS. 7 and 8.

Figure 8:
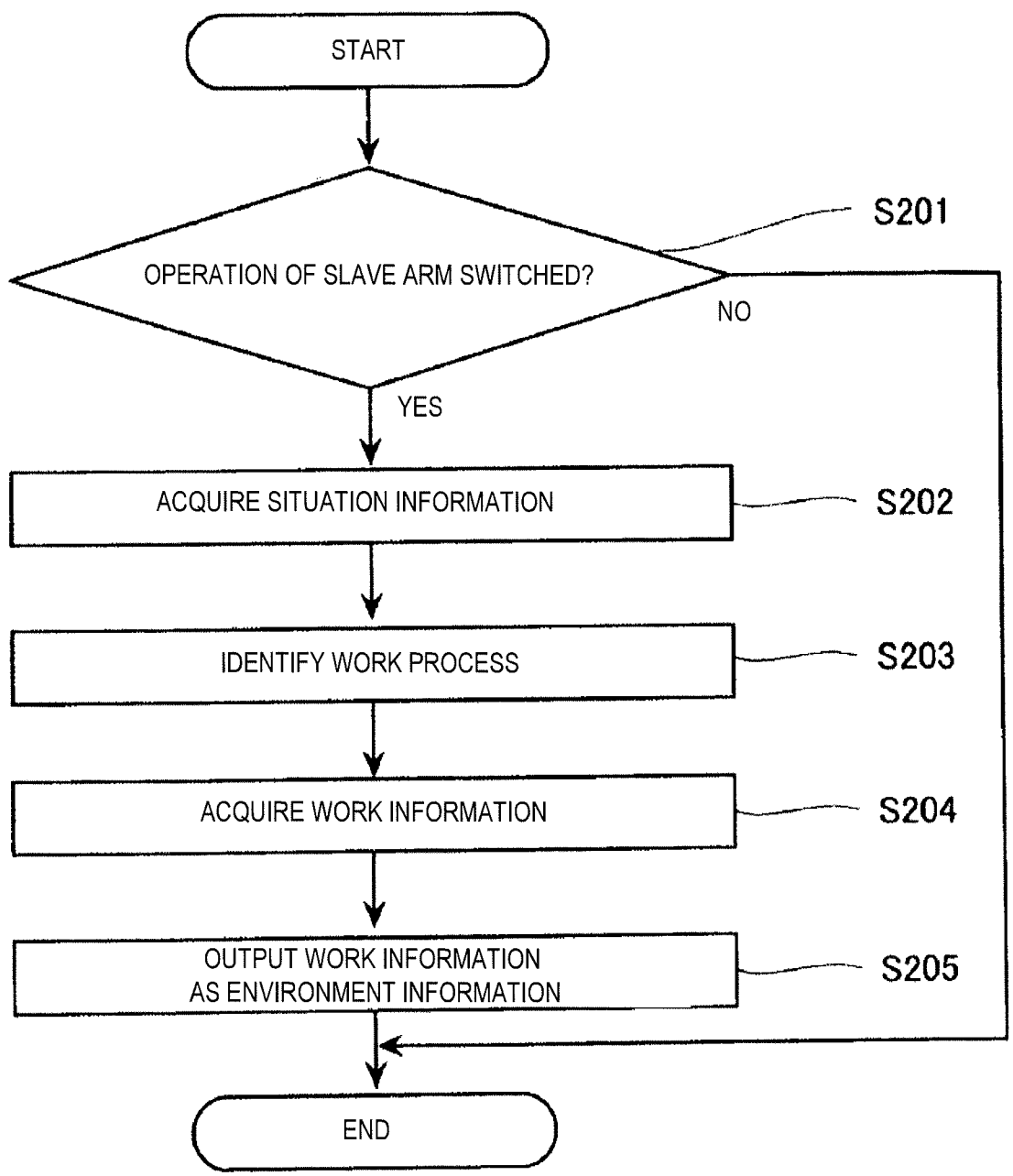
FIG. 8 is a flowchart illustrating operation of the remote-control manipulator system according to the fourth embodiment.

FIG. 8 is a flowchart illustrating operation of the remote-control manipulator system 100 according to the fourth embodiment. Note that, the following operation is executed by the arithmetic part of the control device 4 reading the program stored in the memory part or the storage device 5.

As illustrated in FIG. 8, the control device 4 determines whether the operator has switched the operation of the slave arm 1 (Step S201). Specifically, the motion controller 42 of the control device 4 determines whether the information indicating that the operation is switched from a certain slave arm 1 to another slave arm 1, that is, information on a manipulation start instruction for a given slave arm 1, is inputted from the manipulator 2 via the receiver 40.

If the motion controller 42 of the control device 4 determines that the information on the manipulation start instruction is not inputted (NO at Step S201), it ends this program. Note that, when the control device 4 ends this program, it again executes this program, for example, after 50 msec. On the other hand, if the motion controller 42 of the control device 4 determines that the information on the manipulation start instruction is inputted (YES at Step S201), it executes processing illustrated at Step S202.

At Step S202, the control device 4 acquires the situation information acquired by the situation information acquisition device 3. Specifically, the receiver 40 receives the situation information on the given slave arm 1 acquired by the situation information acquisition device 3, and the motion controller 42 acquires the received situation information.

Next, based on the situation information acquired at Step S202, the motion controller 42 of the control device 4 identifies, when the given slave arm 1 is in operation, the process currently executed by the given slave arm 1 or, when the given slave arm 1 is in a manipulating instruction input standby state (manipulation standby state), the process executed immediately previously (Step S203).

Note that the motion controller 42 of the control device 4 may identify the information on the process currently executed by the given slave arm 1 or the information on the process executed immediately previously from the motion controller 42. In this case, the motion controller 42 constitutes the situation information acquisition device. Further, when the motion controller 42 constitutes the situation information acquisition device, Step S202 may be omitted.

Next, the control device 4 acquires the work information relating to the next identification to the process identified at Step S203 from the work information 53 in the storage device 5 (Step S204). Specifically, the motion controller 42 of the control device 4 acquires the process subsequent to the process identified at Step S203 from the operation sequence information 51 in the storage device 5, and acquires the work information relating to the subsequent process from the work information 53 in the storage device 5.

For example, if the process identified at Step S203 is a welding process and the subsequent process is a painting process, the motion controller 42 of the control device 4 acquires information, such as sound generated when the slave arm 1 is painting, smell of the paint, the color of the paint (light reflected on the paint) etc., as the work information.

Next, the control device 4 outputs the work information acquired at Step S204 to the environment reproducing device 6 as the environment information (Step S205). Specifically, the motion controller 42 of the control device 4 outputs the work information acquired at Step S204 to the environment reproducing device 6 via the output controller 43 as the environment information.

Thus, the environment reproducing device 6 is capable of reproducing the environment information corresponding to the situation of the process which the given slave arm 1 executes next and notifying it to the operator.

In the remote-control manipulator system 100 according to the fourth embodiment configured as described above, in order to reproduce the environment information corresponding to the situation in the process which the given slave arm 1 executes next, the operator can grasp the process which the given slave arm 1 executes next more specifically compared with the remote-control manipulator system according to first embodiment.

Therefore, in the remote-control manipulator system 100 according to the fourth embodiment, the operator becomes easier to focus on the remote-controlling work, mistakes of operation are reduced, and fatigue of the operator is reduced compared with the remote-control manipulator system according to first embodiment. Moreover, the work efficiency of the remote control is improved.

Note that in the fourth embodiment, although a form in which whether the operation of the slave arm 1 is switched is determined at Step S201 is adopted, it is not limited to this. Similarly to the second embodiment, a form in which whether the acquiring instruction is inputted from the instruction acquisition device 7 is determined may be adopted, or similarly to the third embodiment, a form in which whether to start operation of a given slave arm 1, whether the operation of the given slave arm 1 is ended, etc. is determined may be adopted.

It is apparent for a person skilled in the art that many improvements or other embodiments of the present disclosure are possible from the above description. Therefore, the above description is to be interpreted only as illustration, and it is provided in order to teach a person skilled in the art the best mode in which the present disclosure is implemented. Details of the structures and/or functions of the present disclosure may be substantially changed without departing from the spirit of the present disclosure.

INDUSTRIAL APPLICABILITY

Since it is possible to intuitively grasp the current situation of the slave arm to be manipulated with the remote-control manipulator system and the method of operating the same of the present disclosure, they are useful in the field of industrial robots.

DESCRIPTION OF REFERENCE CHARACTERS

1 Slave Arm
2 Manipulator

3 Situation Information Acquisition Device
4 Control Device
5 Storage Device
6 Environment Reproducing Device
7 Instruction Acquisition Device
21 Desk
22 Chair
40 Receiver
41 Environment Information Acquirer
42 Motion Controller
43 Output Controller
44 Work Information Acquirer
51 Operation Sequence Information
52 Environment Information
53 Work Information
61 Display Device
62 Speaker
63 Spray Can
64 Lighting Device
65 Vibration Device
66 Posture Changing Device
67 Air Conditioner
100 Remote-control Manipulator System

The invention claimed is:

1. A remote-control manipulator system comprising:
a manipulator configured to receive a manipulating instruction from an operator;
a slave arm installed in a workspace, the slave arm being configured to perform a series of operations including a plurality of processes;
a situation information acquisition device configured to acquire situation information indicating a situation of the slave arm in the workspace;
an environment reproducing device configured to reproduce, in a space where the manipulator is installed, environment information relating to an environment in the workspace;
a control device configured to cause the environment reproducing device to reproduce the environment information corresponding to the situation information outputted from the situation information acquisition device; and
a storage device storing work information relating to each process of the plurality of processes performed by the slave arm,
wherein the control device is configured to (i) identify a first process of the plurality of processes currently executed by the slave arm based on the situation information and (ii) cause the environment reproducing device to reproduce, as the environment information, the work information relating to a second process subsequent to the identified first process, in the space where the manipulator is installed,
wherein the situation information is at least one of a group comprised of (i) image information in the workspace, (ii) information on sound generated in the workspace, (iii) information on smell generated in the workspace, (iv) information on light generated in the workspace, (v) information on a temperature in the workspace, and (vi) information on vibration generated in the workspace,
wherein the work information is at least one of a group comprised of (i) image information in the workspace, (ii) information on sound generated in the workspace, (iii) information on smell generated in the workspace, (iv) illumination information, (v) information on a temperature in the workspace, (vi) information on vibration generated in the workspace, and (vii) information on an operator's posture, and
wherein the control device is configured to cause the environment reproducing device to reproduce, as the environment information, information different from the situation information in the space where the manipulator is installed.

2. The remote-control manipulator system of claim 1, further comprising a plurality of slave arms including the slave arm,
wherein the control device is configured to cause the situation information acquisition device to acquire the situation information when the operation of the slave arm is switched by the manipulator.

3. The remote-control manipulator system of claim 1, further comprising an instruction acquisition device configured to receive an acquiring instruction for the situation information from the operator and output the acquiring instruction to the control device,
wherein the control device is configured to cause the situation information acquisition device to acquire the situation information when the acquiring instruction is inputted from the instruction acquisition device.

4. The remote-control manipulator system of claim 1, wherein the control device is configured to cause the situation information acquisition device to acquire the situation information when at least one process of the plurality of processes is to be started or once at least one process is ended.

5. A method of operating a remote-control manipulator system including a manipulator configured to receive a manipulating instruction from an operator, and a slave arm installed in a workspace and configured to perform a series of operations including a plurality of processes, the method comprising:
(A) acquiring situation information indicating a situation of the slave arm in the workspace;
(B) causing an environment reproducing device to reproduce environment information corresponding to the situation information acquired in the acquiring (A), in a space where the manipulator is installed; and
(A1) identifying a first process currently executed by the slave arm,
wherein the causing (B) includes causing the environment reproducing device to reproduce, as the environment information, work information relating to a second process subsequent to the first process identified in the identifying (A1),
wherein the situation information is at least one of a group comprised of (i) image information in the workspace, (ii) information on sound generated in the workspace, (iii) information on smell generated in the workspace, (iv) information on light generated in the workspace, (v) information on a temperature in the workspace, and (vi) information on vibration generated in the workspace,
wherein the work information is at least one of a group comprised of (i) image information in the workspace, (ii) information on sound generated in the workspace, (iii) information on smell generated in the workspace, (iv) illumination information, (v) information on a temperature in the workspace, (vi) information on vibration generated in the workspace, and (vii) information on an operator's posture, and wherein the causing (B) includes causing the environment reproducing device to reproduce, as the environment information, information different from the situation information.

6. The method of operating the remote-control manipulator system of any claim 5, wherein:
the remote-control manipulator system further includes a plurality of slave arms including the slave arm, and
the acquiring (A) is executed when the operation of the slave arm of the plurality of slave arms is switched by the manipulator.

7. The method of operating the remote-control manipulator system of claim 5, wherein:
the remote-control manipulator system further includes an instruction acquisition device configured to (i) receive an acquiring instruction for the situation information from the operator and (ii) output the acquiring instruction, and
the acquiring (A) is executed when the acquiring instruction is outputted from the instruction acquisition device.

8. The method of operating the remote-control manipulator system of claim 5, wherein the acquiring (A) is executed when at least one process of the plurality of processes is to be started or once at least one process is ended.

* * * * *